(12) United States Patent
Hart

(10) Patent No.: US 8,282,656 B2
(45) Date of Patent: Oct. 9, 2012

(54) SUTURE PASSING INSTRUMENT

(75) Inventor: Rickey Hart, Marco Island, FL (US)

(73) Assignee: Karl Storz GmbH & Co. KG (DE)

( * ) Notice: Subject to any disclaimer, the term of this patent is extended or adjusted under 35 U.S.C. 154(b) by 574 days.

(21) Appl. No.: 12/473,998

(22) Filed: May 28, 2009

(65) Prior Publication Data

US 2010/0305581 A1    Dec. 2, 2010

(51) Int. Cl.
*A61B 17/10* (2006.01)
*A61B 17/04* (2006.01)
*A61B 17/00* (2006.01)

(52) U.S. Cl. ........ 606/145; 606/139; 606/144; 606/148; 606/205

(58) Field of Classification Search ........... 606/139, 606/144, 148, 205, 145, 216; 112/169
See application file for complete search history.

(56) References Cited

U.S. PATENT DOCUMENTS

| | | | |
|---|---|---|---|
| 1,856,721 A | 5/1932 | Nagelmann | |
| 4,164,225 A | 8/1979 | Johnson et al. | |
| 4,596,249 A | 6/1986 | Freda et al. | |
| 5,776,150 A * | 7/1998 | Nolan et al. | 606/148 |
| 5,980,538 A | 11/1999 | Fuchs et al. | |
| 6,217,592 B1 | 4/2001 | Freda et al. | |
| 6,770,084 B1 | 8/2004 | Bain et al. | |
| 6,893,448 B2 | 5/2005 | O'Quinn et al. | |
| 6,896,686 B2 * | 5/2005 | Weber | 606/145 |
| 6,984,237 B2 | 1/2006 | Hatch et al. | |
| 7,112,208 B2 | 9/2006 | Morris et al. | |
| 7,381,212 B2 | 6/2008 | Topper et al. | |
| 2004/0199184 A1 * | 10/2004 | Topper et al. | 606/144 |
| 2007/0270885 A1 | 11/2007 | Weinert et al. | |
| 2008/0097482 A1 | 4/2008 | Bain et al. | |

OTHER PUBLICATIONS

European Search Report; Application No. EP 10 16 4237; Sep. 22, 2010; 6 pages.

* cited by examiner

*Primary Examiner* — Corrine M McDermott
*Assistant Examiner* — Melissa Ryckman
(74) *Attorney, Agent, or Firm* — St. Onge Steward Johnston & Reens LLC (57) ABSTRACT

A method for passing suture through tissue and a suture passing instrument having a first jaw coupled to an end of an elongated shaft, a second jaw coupled to the first jaw, and formed with a holder for supporting a suture, and a needle slidably disposed within the first jaw, having a hook on a side for releasably capturing a portion of a suture, is provided. The first jaw defines a channel for receiving the needle and a ramp for deflecting the needle transversely of the shaft when advanced to an extended position.

38 Claims, 9 Drawing Sheets

SUTURE PASSING INSTRUMENT

FIELD OF THE INVENTION

The invention relates to suture passing surgical instruments. More specifically, the invention relates to a hand instrument and method for passing suture through tissue.

BACKGROUND OF THE INVENTION

Arthroscopic surgery often requires a surgeon to attach a length of suture material remotely to an internal body part. For example, a suture is passed through a detached tendon and is then secured to a hole or anchored in a bone. Various instruments have been developed for this purpose, many of them having an elongate configuration and low profile for facilitating use through cannulas in less invasive surgery. These devices have also typically have opposing jaws, which clamp onto either side of the tissue to be sutured. However, the various known mechanisms and configurations for loading the suture, grasping the suture, and threading a suture between the jaws shown in these prior art devices are exceedingly complex. Moreover, due to this complexity and poor design, in general, these devices have a tendency to create tangles in the suture or to simply fail to pass the suture through the tissue as intended. Many of these devices may also require the use of both hands to operate the instrument.

What is desired, therefore, is a suture passing device having a low profile that can accommodate many thicknesses of tissue, is easy to load with a suture and utilizes a mechanism that is easy and reliable for threading the suture through tissue.

SUMMARY OF THE INVENTION

Accordingly, it is an object of the present invention to provide a suture passing instrument that is of simple configuration so that a suture may be loaded into the instrument with relative ease. It is a further object of the present invention to provide a suture passing instrument having wide opening jaws so that it may be used with a range of tissue thickness. It is a further object of the invention to provide a suture passing instrument which prevents tangling of the suture and only threads one loop of suture through the tissue as desired. A further object of the invention is to provide a suture passing instrument which may be operated with one hand.

These and other objectives are achieved by providing a suture passing instrument comprising a first jaw coupled to an end of an elongated shaft, a second jaw coupled to the first jaw, and formed with a holder for supporting a suture, and a needle slidably disposed within the first jaw, the needle having a hook on a side for releasably capturing a portion of a suture. The first jaw defines a channel for receiving the needle and a ramp for deflecting the needle transversely of the shaft when advanced to an extended position. In some embodiments, the first jaw is stationary and the second jaw is movable and may be pivotally coupled to the first jaw. The needle may be made from a malleable material and may have a sharp distal tip for piercing tissue. An opening may also be formed in the second jaw that provides a clearance for a tip portion of the needle to pass when it is advanced to its extended position.

In some embodiments, the opening and the holder may be aligned such that a suture received in the holder extends across the opening. In further embodiments, the holder supports the suture on an inner surface of the movable jaw facing the stationary jaw. The holder may comprise at least one slot formed on an edge of the movable jaw which, in further embodiments, may comprise a first slot formed on a distal edge of the movable jaw and a second slot formed on an adjacent edge of the movable jaw. The second slot may be T-shaped. In further embodiments, a plurality of needles may be slidably disposed within the first jaw. In yet further embodiments, the elongated shaft may be semi-rigid or hinged.

Other objects of the present invention are achieved by provision of a suture passing instrument comprising a stationary jaw coupled to an elongated shaft, a malleable needle slidably disposed within the stationary jaw, the needle having a distal tip and a hook on an edge for releasably capturing a portion of a suture, a movable jaw pivotally coupled to the stationary jaw, and formed with a holder for supporting a suture and an opening that provides a clearance through which a tip portion of the needle passes when in its extended position, a first actuating member coupled to the movable jaw for moving it between a closed position alongside the stationary jaw and an open position spaced therefrom, and a second actuating member coupled to said needle for moving the needle between a recessed position and an extended position wherein the distal tip of the needle is deflected by the ramp and extends out of the stationary jaw transversely of the shaft such that the needle tip enters the opening in the movable jaw and the needle hook captures a portion of the suture supported in the holder. The stationary jaw may define an internal channel for receiving the needle and a distal ramp.

Other objects of the present invention are achieved by provision of a method of passing suture comprising the steps of providing a suture passing instrument having a first jaw coupled to an elongated shaft, a second jaw coupled to the first jaw, and formed with a holder for supporting a suture, and a needle slidably disposed within the first jaw, the needle having a hook on a side for capturing a portion of a suture; loading a suture into the holder of said second jaw; grasping tissue between said first jaw and second jaw; and passing suture through said tissue by advancing said needle to its extended position, capturing a portion of the suture supported in the holder with the hook, and returning the needle to a recessed position so that a loop of the suture portion captured by the needle is drawn through the tissue. The first jaw may define a channel for receiving the needle and a distal ramp for deflecting the needle transversely of the shaft when advanced to an extended position.

In some embodiments, the step of grasping tissue between the first jaw and second jaw further includes actuating a first actuating member displaced within the shaft and coupled to the second jaw such that the second jaw pivots toward the first jaw to grasp tissue therebetween. In further embodiments, the step of advancing the needle further includes actuating a second actuating member displaced within the shaft and coupled to the needle such that the distal tip of the needle is advanced proximally, is deflected by the ramp and extends out of the first jaw transversely of the shaft. The step of advancing the needle may include advancing the needle through tissue. In still further embodiments, the step of advancing the needle includes advancing the needle such that the needle tip enters the opening in the second jaw.

Other objects of the invention and its particular features and advantages will become more apparent from consideration of the following drawings and accompanying detailed description.

DETAILED DESCRIPTION OF THE INVENTION

Figure 1:
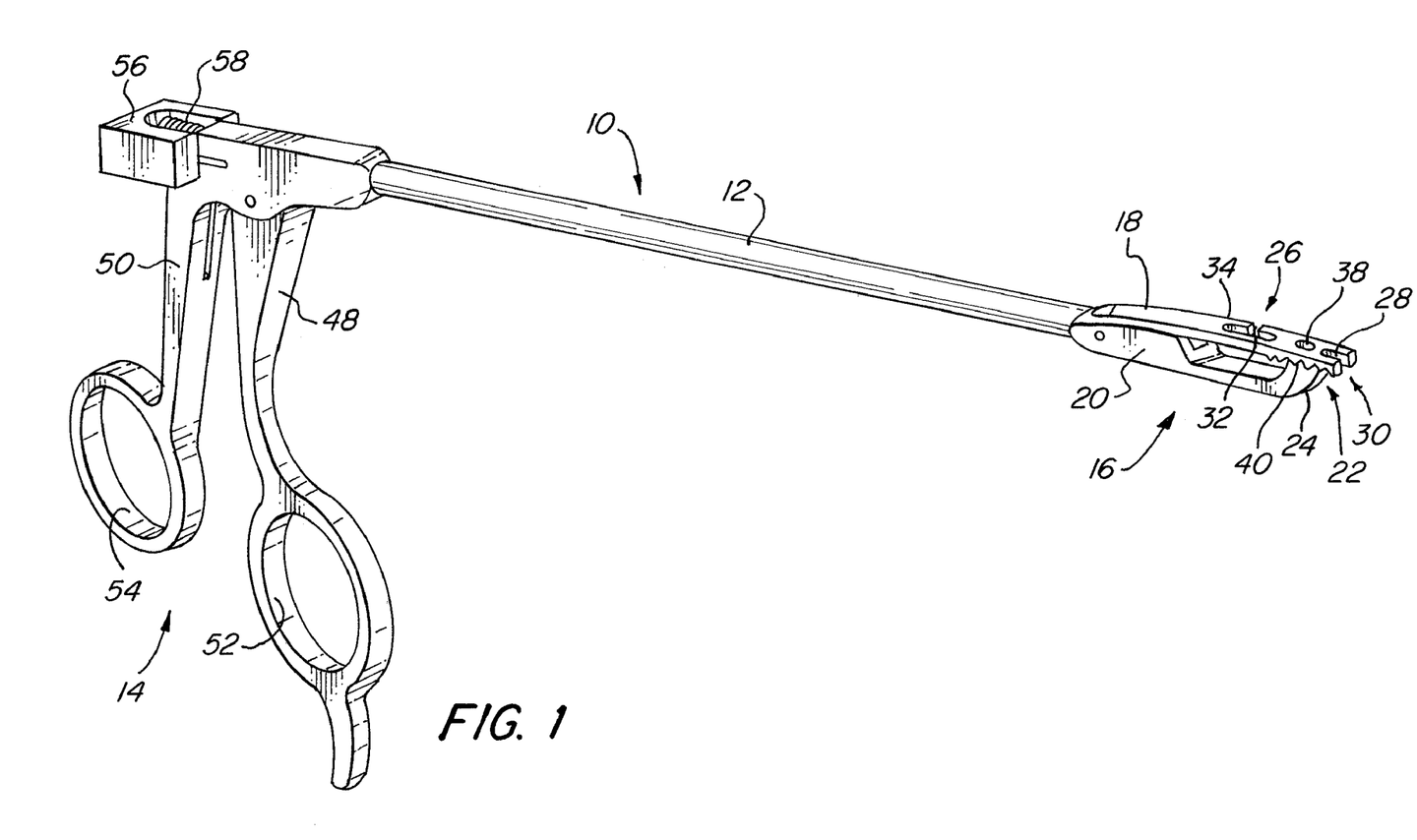
FIG. 1 is a perspective view of one embodiment of the suture passing instrument of the present invention.

One embodiment of the suture passing instrument 10 of the present invention is shown in FIG. 1. Suture passing instrument 10 includes a shaft 12 connecting a proximally disposed handle portion 14 to a distally disposed jaw portion 16. Shaft 12 may be semi-rigid or hinged along its length so that it can be bent or angled once the suture passing instrument 10 is inserted in a trocar (not shown). This allows a user to adjust the jaw portion 16 at different angles to reach the desired area. Jaw portion 16 includes an upper jaw 18 pivotally connected to a stationary lower jaw 20, which may be formed integral with the shaft 12. Alternatively, upper jaw 18 may be pivotally connected directly to the shaft 12. The distal end 22 of lower jaw 20 is provided as a curved portion 24.

Figure 2:
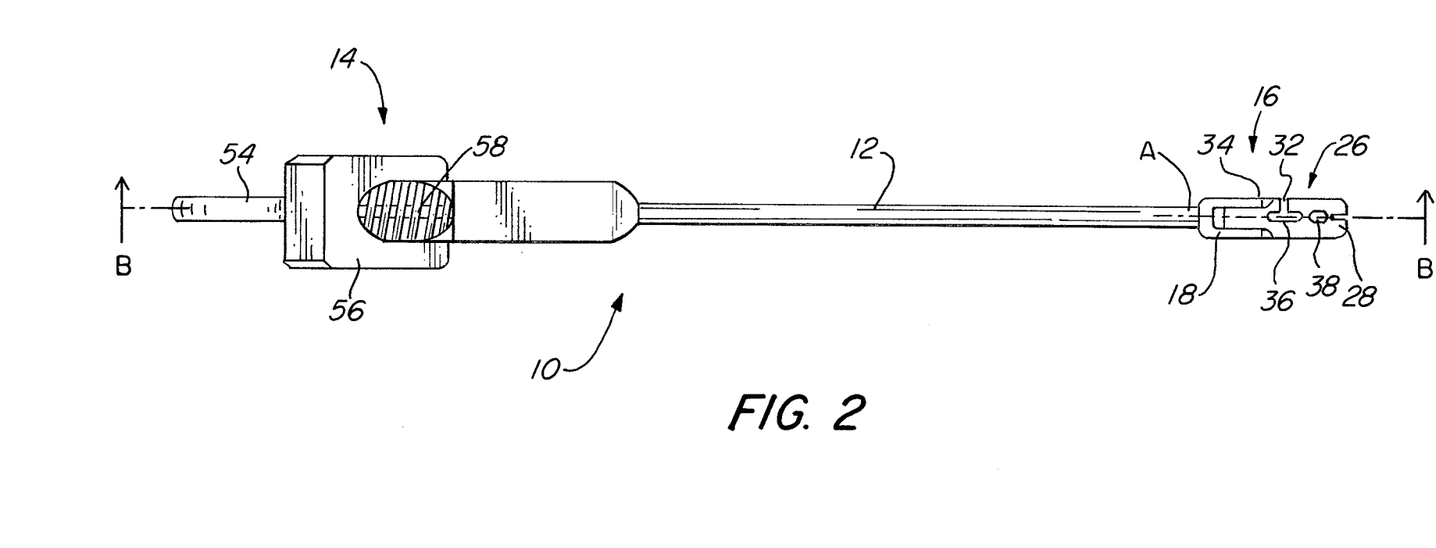
FIG. 2 is a top view of one embodiment of the suture passing instrument of the present invention.
Figure 3:
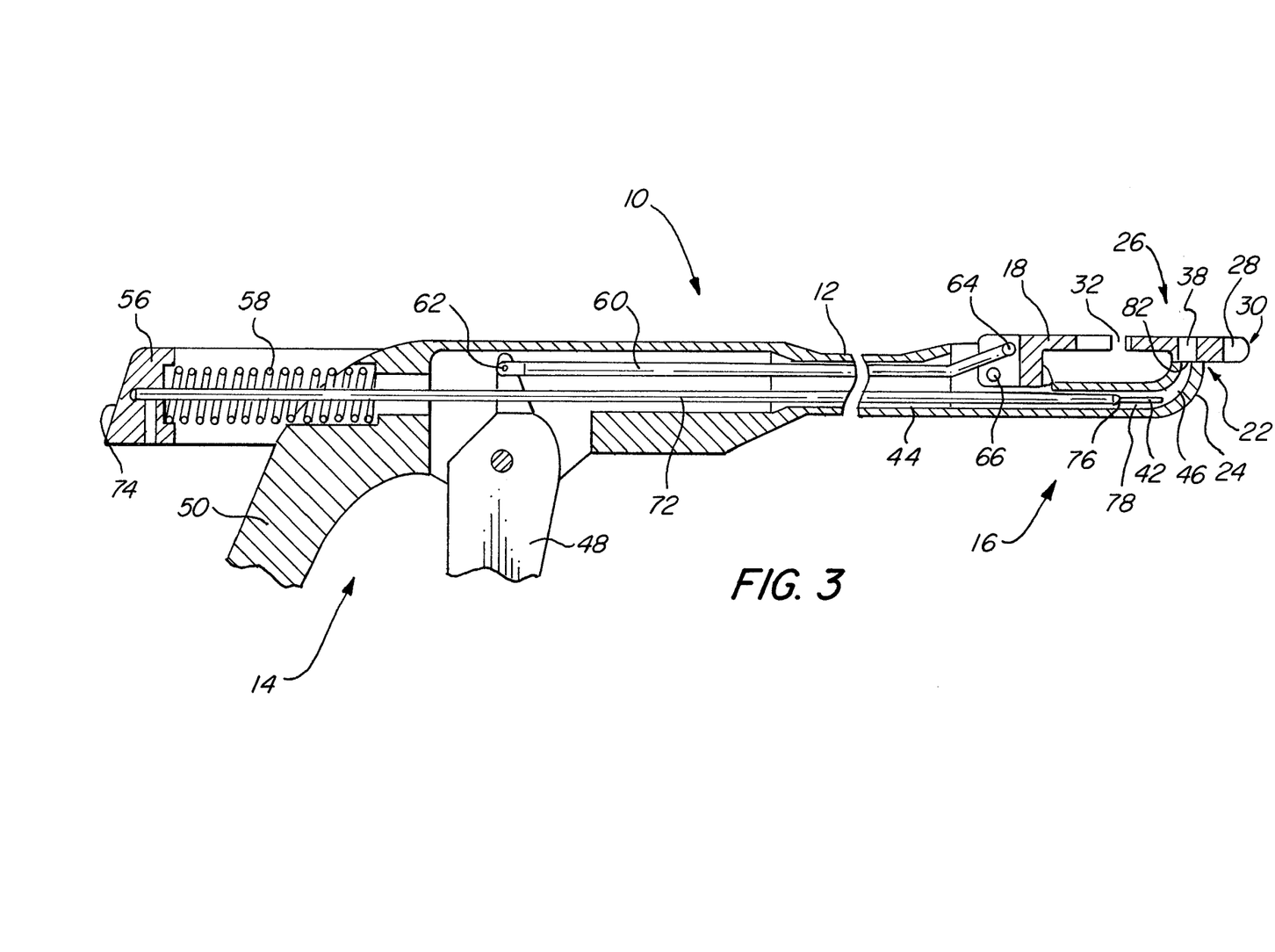
FIG. 3 is a sectional side view of one embodiment of the suture passing instrument of the present invention, taken along line B.

As shown in FIGS. 2 and 3, upper jaw 18 includes a holder 26, which comprises at least one slot, for supporting a suture (not shown). In the present embodiment, the holder 26 comprises a first slot 28 formed on the distal edge 30 of the upper jaw 18 and a second slot 32 formed on an adjacent edge 34. Second slot 32 may be provided in the shape of a "T", having bar 36, which aids in supporting the suture within the holder. An opening 38 is also provided on second slot 32, the utility of which will be described below. Preferably, bar 36 and the first slot 28 both lie along an axis A. More preferably, bar 36, first slot 28, and opening 38 all lie along axis A. Axis A may, but need not, be the same as axis B, which bisects shaft 12. The inner surface 39 of upper jaw 18 may also be provided with a plurality of ridges 40 to aid in gripping tissue between the jaws.

Suture passing instrument 10 also comprises a needle 42. Preferably, needle 42 is flexible and may be composed of spring stainless steel or nitinol. Depicted in FIG. 7, needle 42 is provided with a sharp tip 90 for piercing tissue and a hook 92 on an edge for capturing a suture, as will be described below. Needle 42 is disposed within an internal channel 44 which runs the length of shaft 12 and continues into the lower jaw 20. Corresponding to the curved portion 24 of lower jaw 20, internal channel 44 is provided with a ramp 46, the utility of which will be explained below. In additional embodiments, multiple needles may be disposed within internal channel 44, or individually within multiple channels. Accordingly, upper jaw 18 would be provided with multiple holders for supporting a suture so that multiple suture loops could be passed at one time.

Figure 4:
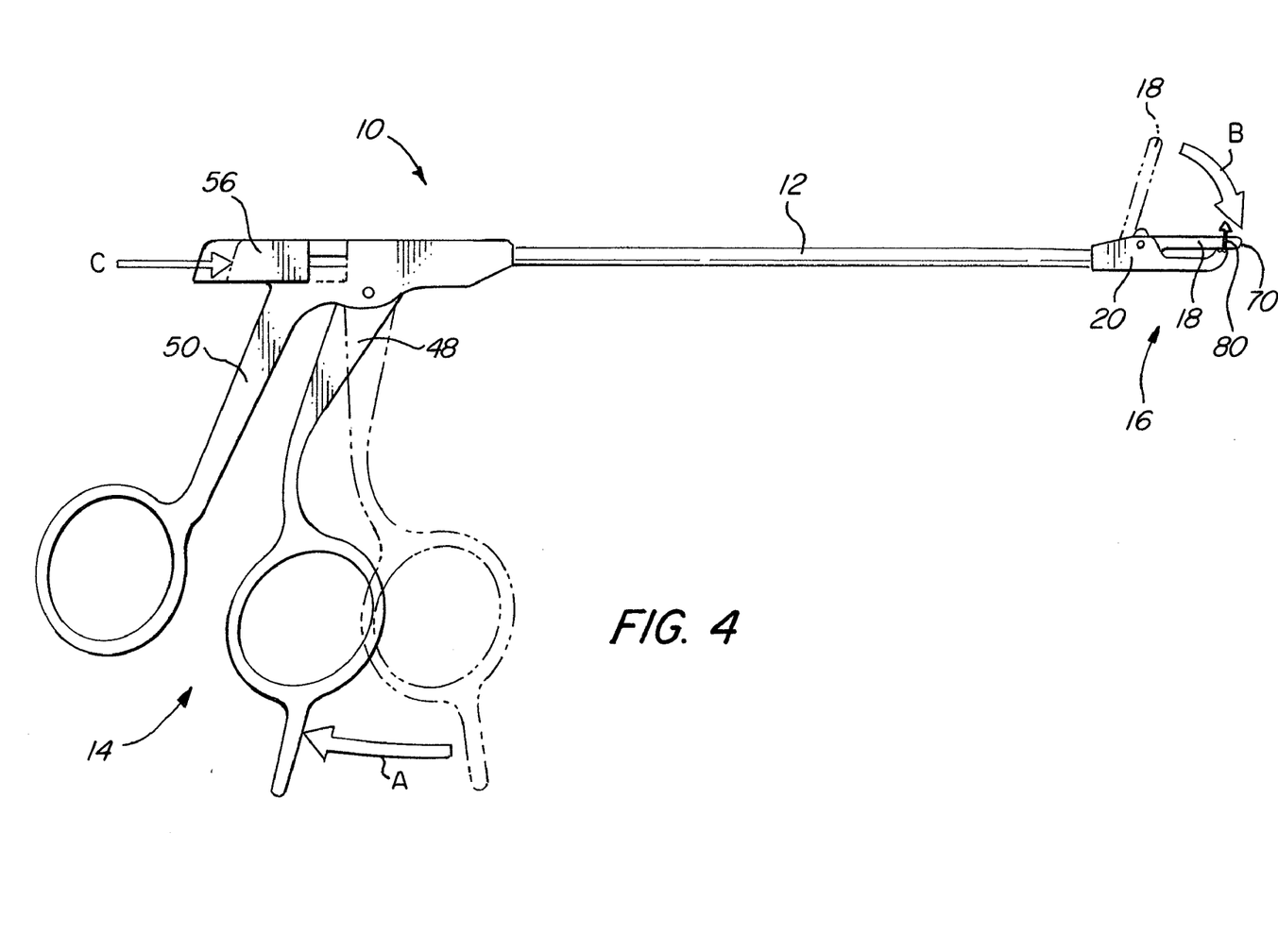
FIG. 4 is a side view of one embodiment of the suture passing instrument of the present invention.

Handle portion 14 comprises a trigger arm 48 and a stationary arm 50, both terminating in finger grips 52, 54, and a spring loaded push button 56. Spring 58 biases push button 56 in an inactive position. As shown in FIG. 3, a first actuator 60 is coupled at a proximal end 62 to trigger arm 48 and at a distal end 64 to upper jaw 18. When trigger arm 48 is moved in the direction of arrow A (shown in FIG. 4), upper jaw 18 pivots around pivot point 66 in the direction of arrow B from an open position 68 to a closed position 70. This allows for a user to grasp an object, namely tissue, between the jaws 18, 20 by squeezing trigger arm 48. Moreover, the ample clearance provided when upper jaw 18 is in the open position 68 allows a user to grasp tissue of many thicknesses.

A second actuator 72 is coupled at a proximal end 74 to push button 56 and at a distal end 76 to needle 42. Depressing push button 56 in the direction of arrow C, distally advances needle 42 from a recessed position 78 (shown in FIG. 3) to an extended position 80 (shown in FIG. 4), where it extends out of outlet 82 to channel 44. Ramp 46 deflects needle 42 so that it exits channel 44 transverse of the shaft 12. As shown in FIG. 3, outlet 82 is vertically aligned with opening 38 when upper jaw 18 is in its closed position 70. Thus, when needle 42 is in its extended position, it extends into opening 38. Both first 60 and second 72 actuators are disposed within internal channel 44.

Notably, a user can grasp the instrument and actuate trigger arm 52 with the fingers of one hand through finger loops 52, 54, leaving the thumb free to actuate push button 56 so that only one hand is necessary to operate the instrument. This leaves the user's other hand free to manipulate the suture threaded in the tissue or to perform other tasks.

Figure 5:
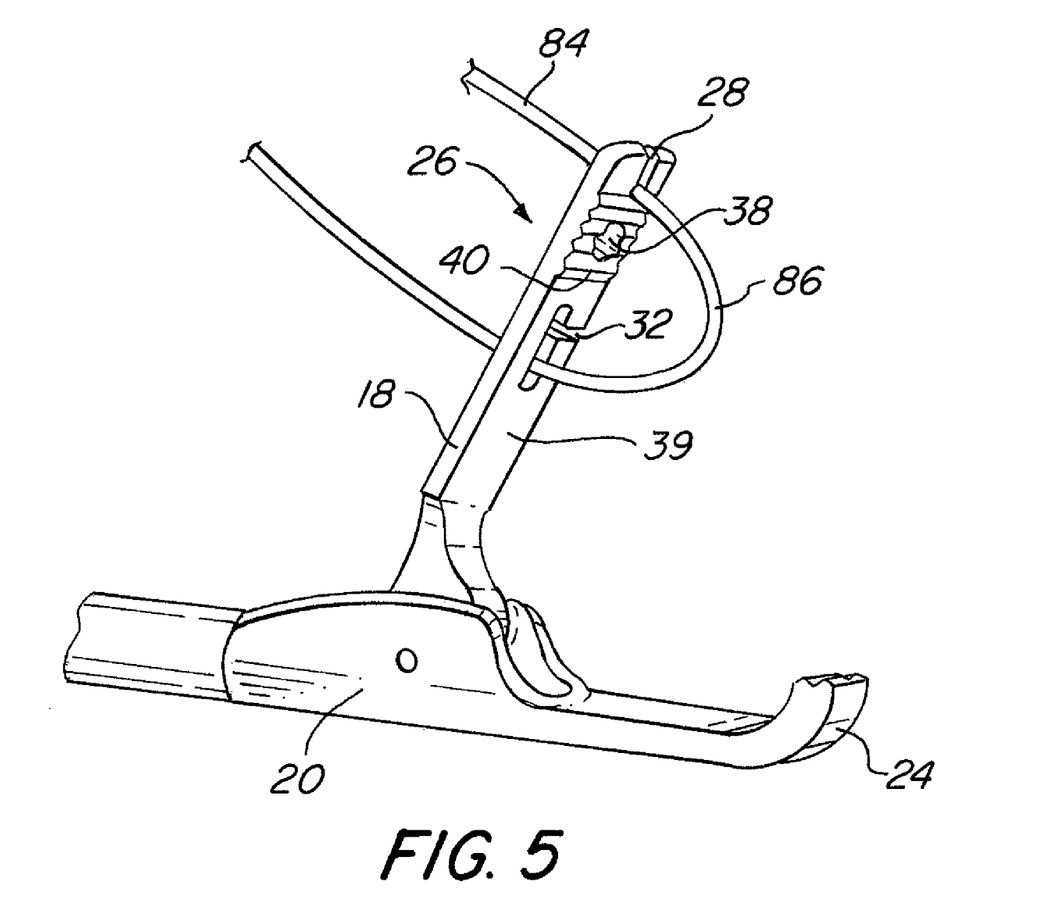
FIG. 5 is a perspective view of the jaw portion of one embodiment of the suture passing instrument of the present invention.
Figure 6:
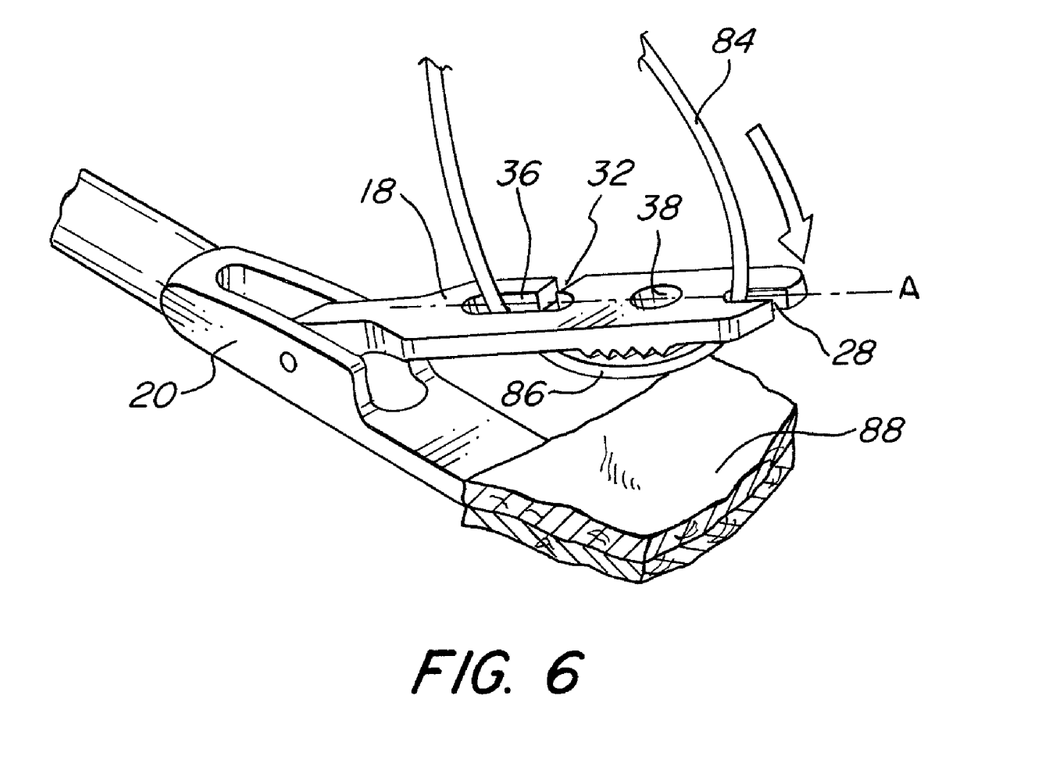
FIG. 6 is a perspective view of the jaw portion of one embodiment of the suture passing instrument of the present invention.

In operation, a suture 84 is first loaded into holder 26 by sliding it into first 28 and second 32 slots, as shown in FIG. 5, so that a portion 86 of suture 84 lies across the inner surface 39 of upper jaw 18. As noted above, bar 36, first slot 28, and opening 38 preferably lie along a single axis A so that suture portion 86 lies squarely across opening 38. Jaws 18, 20 are then placed on either side of tissue 88 intended to be sutured. Upper jaw 18 is moved into a closed position 70, as shown in FIG. 6, clamping the tissue 88 between the lower and upper jaws.

Figure 7:
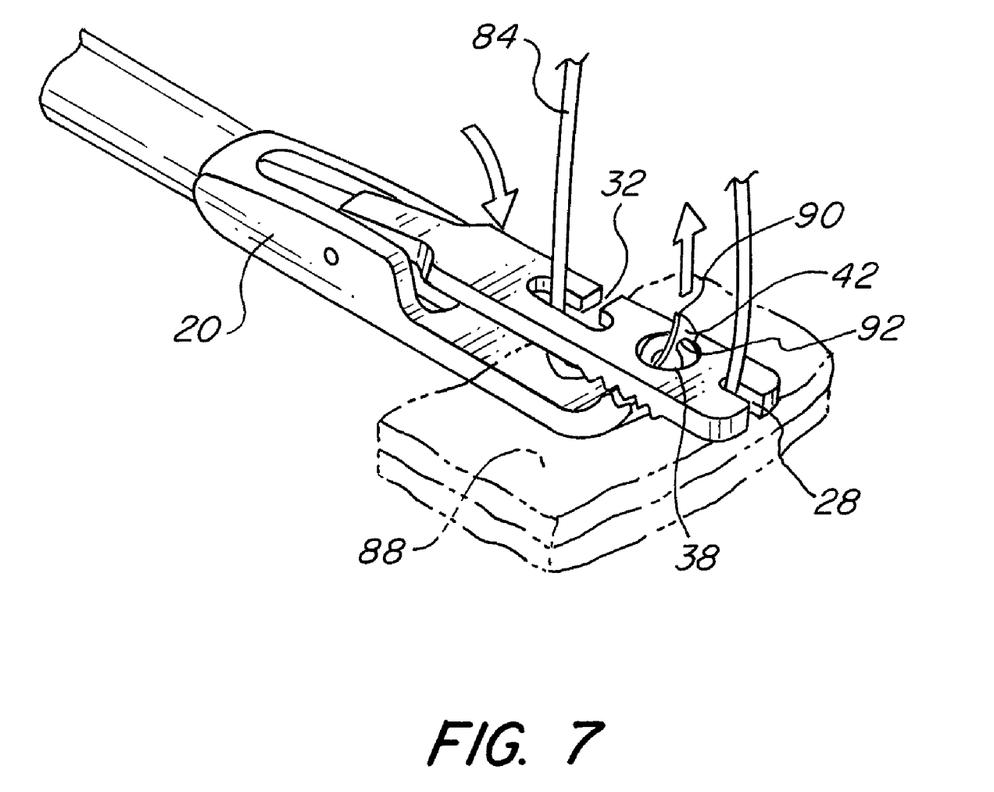
FIG. 7 is a perspective view of the jaw portion of one embodiment of the suture passing instrument of the present invention.
Figure 8:
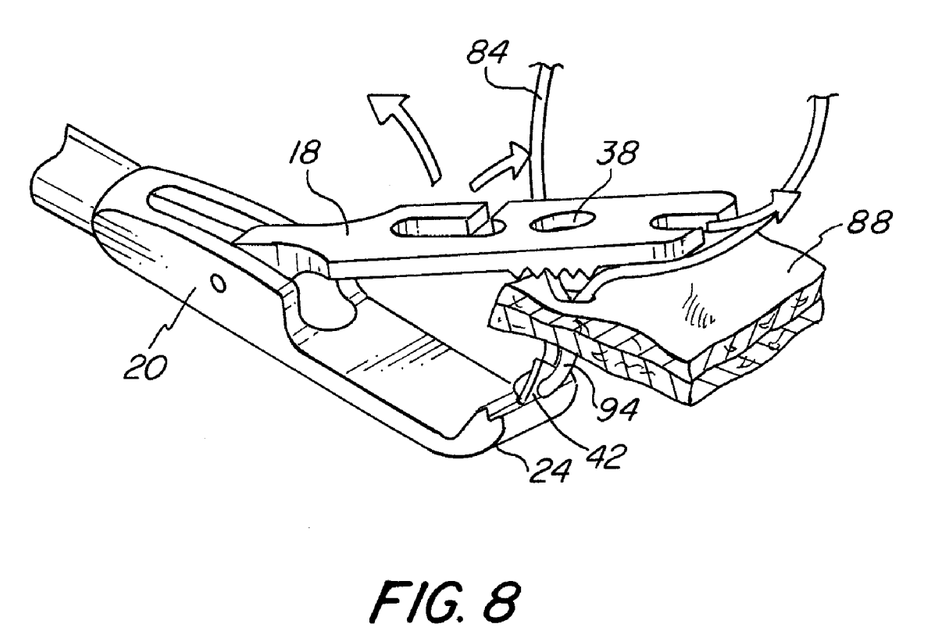
FIG. 8 is a perspective view of the jaw portion of one embodiment of the suture passing instrument of the present invention.
Figure 9:
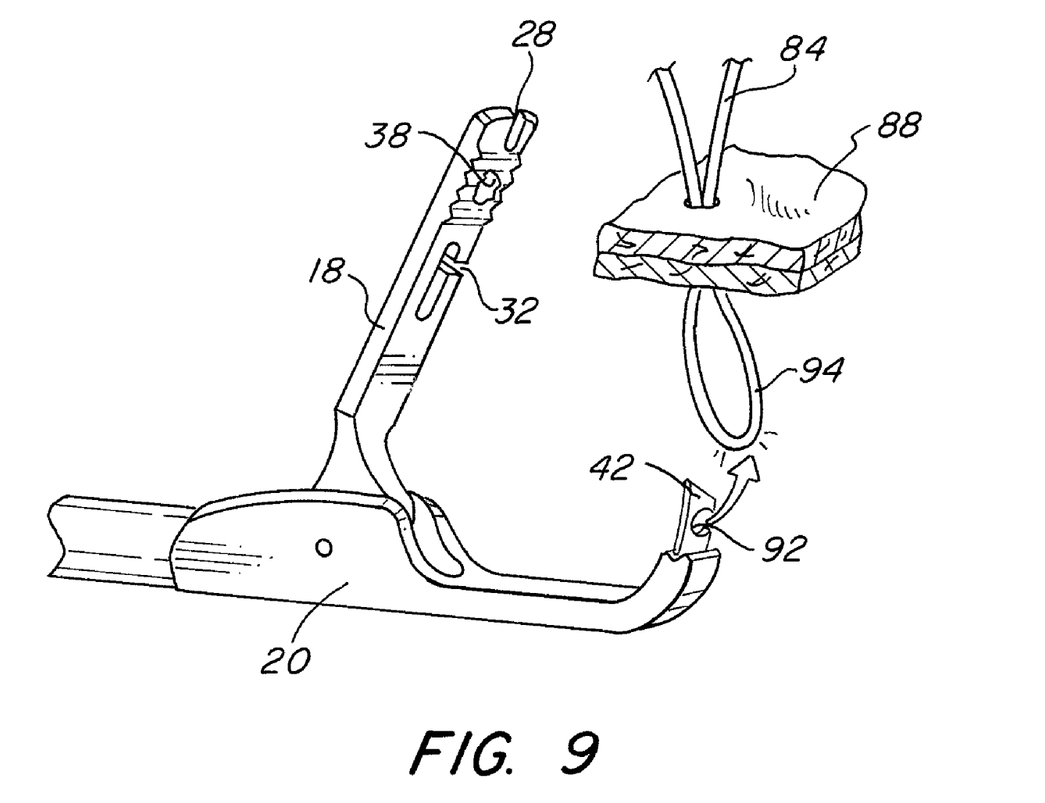
FIG. 9 is a perspective view of the jaw portion of one embodiment of the suture passing instrument of the present invention.

Needle 42 is advanced to its extended position 80, piercing tissue 88 as it passes through outlet 82 and into opening 34, passing by suture portion 86 (shown in FIG. 7). When push button 56 is released, needle 42 then withdraws back through opening 38 and hook 92 catches suture portion 86. As shown in FIG. 8, as needle 42 continues to recede in a proximal direction, suture portion 86 is threaded through tissue 88 forming a suture loop 94. The suture portion 86 is held by the hook 92 against the distal end 22 of lower jaw 20 as the user opens the jaws 18, 20 to release the tissue 88. The trailing ends of suture 84 are then released from holder 26 and the suture loop 94 is released by advancing needle 42 until the suture can clear the hook 92 (FIG. 9). If desired, the user may pull one side of the suture loop 94 through the tissue 88 so that one end of the suture lies on either side of the tissue.

Notably, the length and configuration of the needle 42 is such that it only passes into opening 34 far enough to capture suture portion 86. If needle 42 were allowed to advance such that all of hook 92 extended through opening 34, it would be more likely to capture another portion of suture 84 in addition to suture portion 86. This would cause the suture 84 to become tangled and or for more than one suture portion to be passed through the tissue, which is undesirable.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A suture passing instrument comprising:
    a first jaw coupled to an end of an elongated shaft;
    a second jaw coupled to the first jaw, and formed with a holder for supporting a suture;
    a needle slidably disposed within the first jaw, said needle having a hook on a side for releasably capturing a portion of a suture;
    said first jaw defining a channel for receiving said needle and a ramp for deflecting the needle transversely of the shaft when advanced to an extended position;
    said holder having a first portion and a second portion, said holder first portion comprising a longitudinal slot passing through a distal end of said second jaw and said holder second portion comprising a lateral slot passing through an adjacent side of said second jaw; and
    an opening formed in the second jaw that provides a clearance through which a tip portion of the needle passes when it is advanced to its extended position, said opening being positioned between said holder first portion and holder second portion such that a suture received in the holder extends longitudinally across the opening.

2. The suture passing instrument of claim 1 wherein said first jaw is stationary.

3. The suture passing instrument of claim 1 wherein said second jaw is movable.

4. The suture passing instrument of claim 3 wherein said second jaw is pivotally coupled to the first jaw.

5. The suture passing instrument of claim 1 wherein said needle is made from a malleable material.

6. The suture passing instrument of claim 1 wherein said needle has a sharp distal tip for piercing tissue.

7. The suture passing instrument of claim 1 wherein the first jaw and second jaw are configured to receive tissue therebetween.

8. The suture passing instrument of claim 1 wherein said hook does not pass completely through said opening when said needle is advanced to its extended position.

9. The suture passing instrument of claim 1 wherein said holder supports said suture on an inner surface of the second jaw facing the first jaw.

10. The suture passing instrument of claim 1 wherein said lateral slot of said holder second portion is continuous with a second longitudinal slot in said second jaw.

11. The suture passing instrument of claim 10 wherein said second holder portion is T-shaped.

12. The suture passing instrument of claim 1 further comprising a first actuating member displaced within said shaft and coupled to the second jaw for moving it between a closed position alongside said first jaw and an open position spaced therefrom.

13. The suture passing instrument of claim 1 further comprising a second actuating member displaced within said shaft and coupled to said needle for moving said needle between a recessed position and its extended position.

14. The suture passing instrument of claim 1 wherein said elongated shaft is semi-rigid.

15. A suture passing instrument comprising:
    a stationary jaw coupled to an elongated shaft;
    a malleable needle slidably disposed within the stationary jaw, said needle having a distal tip and a hook on an edge for releasably capturing a portion of a suture;
    said stationary jaw defining an internal channel for receiving said needle and a distal ramp;
    a movable jaw pivotally coupled to the stationary jaw, and formed with a holder for supporting a suture and an opening that provides a clearance through which a tip portion of the needle passes when in its extended position;
    said holder having a first portion and a second portion, said holder first portion comprising a longitudinal slot through a distal edge of said movable jaw and said holder second portion comprising a lateral slot through an adjacent side of said movable jaw;
    said opening being positioned between said holder first portion and holder second portion such that a suture received in the holder extends longitudinally across the opening;
    a first actuating member coupled to the movable jaw for moving it between a closed position alongside said stationary jaw and an open position spaced therefrom; and
    a second actuating member coupled to said needle for moving said needle between a recessed position and an extended position wherein the distal tip of the needle is deflected by the ramp and extends out of the stationary jaw transversely of the shaft such that the needle tip enters the opening in the movable jaw and the needle hook captures a portion of the suture supported in the holder.

16. The suture passing instrument of claim 15 wherein said first and second actuating members are disposed within the shaft.

17. The suture passing instrument of claim 15 wherein said needle tip is sharp for piercing tissue.

18. The suture passing instrument of claim 15 wherein the stationary jaw and movable jaw are configured to receive tissue therebetween.

19. The suture passing instrument of claim 15 wherein said hook does not pass completely through said opening when said needle is advanced to its extended position.

20. The suture passing instrument of claim 15 wherein said holder supports said suture on an inner surface of the movable jaw facing the stationary jaw.

21. The suture passing instrument of claim 15 wherein said lateral slot of said holder second portion is continuous with a second longitudinal slot in said movable jaw.

22. The suture passing instrument of claim 21 wherein said second holder portion is T-shaped.

23. The suture passing instrument of claim 15 wherein said elongated shaft is semi-rigid.

24. A method of passing suture comprising the steps of:
    providing a suture passing instrument having:
        a first jaw coupled to an elongated shaft;
        a second jaw coupled to the first jaw, and formed with a holder for supporting a suture;
        said holder having a first portion and a second portion, said holder first portion comprising a longitudinal slot passing through a distal end of said second jaw and said holder second portion comprising a lateral slot passing through an adjacent side of said second jaw;
        a needle slidably disposed within the first jaw, said needle having a hook on a side for capturing a portion of a suture;

said first jaw defining a channel for receiving said needle and a distal ramp for deflecting the needle transversely of the shaft when advanced to an extended position; and an opening formed in the second law that provides a clearance through which a tip portion of the needle passes when it is advanced to its extended position, said opening being positioned between said holder first portion and holder second portion such that a suture received in the holder extends longitudinally across the opening loading a suture into the holder of said second jaw;

grasping tissue between said first jaw and second jaw; and passing suture through said tissue by advancing said needle to its extended position, capturing a portion of said suture supported in said holder with the needle hook, and returning said needle to a recessed position so that a loop of the suture portion captured by the needle is drawn through the tissue.

25. The method of passing suture of claim 24 wherein said first jaw is stationary.

26. The method of passing suture of claim 24 wherein said second jaw is movable.

27. The method of passing suture of claim 26 wherein said second jaw is pivotally coupled to the first jaw.

28. The method of passing suture of claim 24 wherein said needle is made from a malleable material.

29. The method of passing suture of claim 24 wherein the step of grasping tissue between said first jaw and second jaw further includes actuating a first actuating member displaced within the shaft and coupled to the second jaw such that the second jaw pivots toward the first jaw to grasp tissue therebetween.

30. The method of passing suture of claim 24 wherein the step of advancing the needle further includes actuating a second actuating member displaced within said shaft and coupled to said needle such that the distal tip of the needle is advanced proximally, is deflected by the ramp and extends out of the first jaw transversely of the shaft.

31. The method of passing suture of claim 24 wherein the step of advancing the needle includes advancing the needle through tissue.

32. The method of passing suture of claim 24 wherein the step of advancing the needle includes advancing the needle such that the needle tip enters the opening in the second jaw.

33. The method of passing suture of claim 24 wherein said holder supports said suture on an inner surface of the second jaw facing the first jaw.

34. The method of passing suture of claim 24 wherein said lateral slot of said holder second portion is continuous with a second longitudinal slot in said second jaw.

35. The method of passing suture of claim 25 wherein said second holder portion is T-shaped.

36. The method of passing suture of claim 24 wherein said suture passing instrument further comprises a plurality of needles slidably disposed within the first jaw.

37. The method of passing suture of claim 24 wherein said elongated shaft is semi-rigid.

38. The method of passing suture of claim 24 wherein said elongated shaft is hinged.

* * * * *